United States Patent [19]

Denecker et al.

[11] Patent Number: 4,780,540

[45] Date of Patent: Oct. 25, 1988

[54] PROCESS FOR WORKING UP TARS CONTAINING 2-MERCAPTOBENZOTHIAZOLE

[75] Inventors: Gabriel Denecker, Kalmthout; Guido Lahousse, Schoten; Henri Vandebroek, Waasmunster, all of Belgium; Pol Balmelis, Bergisch-Gladbach, Fed. Rep. of Germany

[73] Assignee: Bayer Aktiengesellschaft, Leverkusen, Fed. Rep. of Germany

[21] Appl. No.: 10,462

[22] Filed: Feb. 3, 1987

[30] Foreign Application Priority Data

Feb. 14, 1986 [DE] Fed. Rep. of Germany ....... 3604705

[51] Int. Cl.$^4$ ............................................ C07D 277/72
[52] U.S. Cl. ................................. 548/177; 548/152; 548/176; 564/437
[58] Field of Search ................................. 548/176, 177

[56] References Cited

U.S. PATENT DOCUMENTS

| | | | |
|---|---|---|---|
| 3,031,073 | 4/1962 | Szlatinay | 260/306 |
| 4,061,646 | 12/1977 | Kawaoka | 548/177 |
| 4,192,804 | 3/1980 | Alicot | 548/177 |

FOREIGN PATENT DOCUMENTS

| | | | |
|---|---|---|---|
| 335567 | 9/1930 | United Kingdom | 548/176 |
| 475296 | 11/1937 | United Kingdom | 548/176 |

*Primary Examiner*—Robert Gerstl
*Attorney, Agent, or Firm*—Connolly & Hutz

[57] ABSTRACT

Tar-like residues from the preparation of 2-mercaptobenzothiazole can be used by heating them at temperatures above 200° C. for at least 1 hour and separating off the aniline and benzothiazole thereby formed.

4 Claims, No Drawings

PROCESS FOR WORKING UP TARS CONTAINING 2-MERCAPTOBENZOTHIAZOLE

The invention relates to the working up of tar-like residues which contain 2-mercaptobenzothiazole and remain after the preparation of the product by reaction of aniline, carbon disulphide and sulphur or of benzothiazole and sulphur or of aniline, carbon disulphide, benzothiazole and sulphur at elevated temperature under increased pressure and subsequent extractive purification of the crude reaction product.

The industrial synthesis of 2-mercaptobenzothiazole by reaction of aniline, carbon disulphide and sulphur or of benzothiazole and sulphur or of aniline, carbon disulphide, benzothiazole and sulphur at temperatures in the range from about 220° C. to about 320° C. under pressures of up to about 13 MPa is known.

For purification, after depressurizing and removal of low-boiling constituents, the crude 2-mercaptobenzothiazole is usually taken up in an aqueous inorganic base and is subsequently separated off from the unreacted higher-boiling starting materials and from the various intermediate and secondary components of the synthesis reaction by extraction of the aqueous 2-mercaptobenzothiazole salt solution with organic water-insoluble extracting agents, such as benzene, toluene, xylene or chlorohydrocarbons, and isolated by acidification (German Patent Specification No. 1,941,379 and DE-OS (German Published Specification) No. 2,709,989).

According to DE-OS (German Published Specification) No. 2,652,394 and EP-OS (European Published Specification) No. 464, the crude reaction product of the synthesis reaction is precipitated directly, without using acid,
by stirring in a liquid medium, for example carbon disulphide or chlorohydrocarbons, in which 2-mercaptobenzothiazole is virtually insoluble. The starting materials and the various intermediate and secondary components of the synthesis reaction remain in solution.

It is known that tar-like residues remain when the extract phases obtained in the purification processes described above are distilled up. These residues contain aniline and benzothiazole fractions, which are in general separated off by vacuum distillation and used again as the starting material for the synthesis reaction.

These tars also contain amounts of 2-mercaptobenzothiazole which cannot be ignored. Frequent attempts have been made to use these 2-mercaptobenzothiazole contents.

Thus, U.S. Pat. No. 3,031,073 proposes complete recycling of the tars to the synthesis reaction. This process has the disadvantage, however, that a coloured 2-mercaptobenzothiazole which contains tar components, which cannot be used as such in the vulcanization of rubber mixtures or as a starting material for the synthesis of other thiazole or sulphenamide accelerators and for which as yet no economically operating purification process is known, results.

It has now been found that the tar-like residue can be utilized by subjecting it to heat treatment and separating off the resulting products, aniline and benzothiazole, in a pure form, in particular by vacuum distillation. These products can be used in a customary manner for the preparation of 2-mercaptobenzothiazole.

The present invention thus relates to a process for working up tar-like residues containing 2-mercaptobenzothiazole, which is characterized in that the residue is heated at temperatures above 200° C. for at least one hour and aniline and benzothiazole are isolated from the product mixture.

Preferably, the residue is heated at 240° C. to 310° C. for 2 to 15 hours. The pressure is thereby established spontaneously at about 0.3 to 3 MPa.

In another embodiment of the process according to the invention, the heat treatment is carried out after or during forcing in of hydrogen and/or hydrogen sulphide (about 0.3 to 10 MPa).

For maximum production of aniline and benzothiazole, the aniline and benzothiazole usually available before the heat treatment are preferably at least partly distilled off from the residue to be worked up.

The total yield of aniline and benzothiazole from the conversion and cleavage process is in general 10 to about 40% by weight, based on the tar employed. Smaller yields are obtained at lower temperatures and/or with longer residence times. Higher temperatures lead increasingly to cracking reactions and to the formation of undesirable components, which can scarcely be separated off from the benzothiazole by distillation, for example 2-methylbenzothiazole.

The process according to the invention can be carried out either discontinuously or continuously in all the apparatuses suitable for pressure reactions, for example stirred reactors, multi-chamber reactors and tube reactors.

The resulting product mixture is then fractionated in vacuo. Distillates with a total content of aniline and benzothiazole of at least 98% by weight are thereby obtained as the top product. A tar-like residue, which is usually less viscous than before the heat treatment and can be burned without problems, for example in a Claus furnace for recovery of the sulphur and for utilization of the energy content, remains as the bottom product.

The distillates containing aniline and benzothiazole, can be reacted with carbon disulphide and sulphur, if appropriate together with fresh aniline and/or benzothiazole, in a known manner to give highly pure 2-mercaptobenzothiazole.

2-Mercaptobenzothiazole is used as a vulcanization accelerator for rubber mixtures and as a starting material for benzothiazolesulphenamides, benzothiazolyl disulphide (MBTS) and mercaptobenzothiazole zinc salt (ZMBT).

EXAMPLE 1

1,000 g of a tar-like residue from the extractive purification of crude 2-mercaptobenzothiazole (MBT) according to German Patent Specification No. 1,941,379 with the following constituents:
aniline: 0.3% by weight
benzothiazole: 4.8% by weight
MBT: 14.5% by weight
were heated at 200° to 315° C. under autogenous pressure for 6 to 7 hours. After cooling, the following analytical values and net yields were determined:

| Temperature (°C.) | 200 | 250 | 275 | 300 | 315 |
|---|---|---|---|---|---|
| Reaction time (hours) | 7 | 6 | 7 | 7 | 7 |
| Analysis: | | | | | |
| Aniline (%) | 0.7 | 4.2 | 7.2 | 9.8 | 10.6 |
| Benzothiazole (%) | 4.5 | 8.6 | 16.0 | 16.0 | 13.0 |
| 2-Methylbenzothiazole (%) | 0.6 | 0.1 | 0.1 | 0.7 | 1.5 |

-continued

| Yield* (%) | 0.1 | 7.7 | 18.1 | 20.7 | 18.5 |

*Net yield of aniline + benzothiazole, based on the tar employed

EXAMPLE 2

1,000 g of a tar-like residue with the following constituents:
aniline: 0.8% by weight
benzothiazole: 3.9% by weight
MBT: 14.8% by weight
were heated at 285° C. for 7 hours, on the one hand under autogenous pressure and on the other hand after forcing in an amount of hydrogen or hydrogen sulphide such that a pressure of 1.6–2.1 MPa was established during the heat treatment.
Product mixtures which give the following results were thereby contained:

|  | Autogenous pressure | $H_2$ atmosphere | $H_2S$ atmosphere |
| --- | --- | --- | --- |
| Analysis: |  |  |  |
| Aniline (%) | 6.6 | 11.0 | 9.2 |
| Benzothiazole (%) | 9.0 | 12.0 | 8.9 |
| Yield* (%) | 10.9 | 18.3 | 13.4 |

*Net yield

EXAMPLE 3

1,000 g of the tar-like residue I were heat-treated by the process according to the invention and the product mixture II thereby obtained was subsequently fractionated at 250° C./60 mm Hg (corresponding to 79 hPa). On the one hand about 780 g of a bottom product III of relatively low viscosity and on the other hand 213 g of a top product IV rich in aniline and benzothiazole resulted. The total yield of aniline and benzothiazole (based on the tar I employed) is about 21%, according to the analytical values below:

|  | I | II | III | IV |
| --- | --- | --- | --- | --- |
| Analysis: |  |  |  |  |
| Aniline (%) | 0.7 | 9.1 | 0.1 | 45.1 |
| Benzothiazole (%) | 4.8 | 13.0 | 1.6 | 53.0 |
| 2-Methylbenzothiazole (%) |  | 0.3 | 0.1 | 0.4 |
| MBT (%) | 12.0 |  |  |  |

We claim:
1. A process for preparing 2-mercaptobenzothiazole comprising
   (a) reacting starting materials comprising (1) aniline, carbon disulphide and sulphur, (2) benzothiazole and sulphur or (3) aniline, carbon disulphide, benzothiazole and sulphur, to form crude 2-mercaptobenzothiazole,
   (b) treating the crude 2-mercaptobenzothiazole by extractive purification with an organic water-insoluble extracting agent,
   (c) removing the extracting agent from the resulting tar-like 2-mercaptobenzothiazole-containing residue,
   (d) working up the residue by heating at a temperature of from 240° to 310° C., under a pressure of from 0.3 to 3 MPa, for 2 to 15 hours, in the absence of any substantial amount of the starting material, to form a product mixture,
   (e) separating aniline and benzothiazole from the thus formed product mixture.
2. A process for preparing 2-mercaptobenzothiazole comprising
   (a) reacting starting materials comprising (1) aniline, carbon disulphide and sulphur, (2) benzothiazole and sulphur or (3) aniline, carbon disulphide, benzothiazole and sulphur, to form crude 2-mercaptobenzothiazole,
   (b) treating the crude 2-mercaptobenzothiazole by extractive purification with an organic water-insoluble extracting agent,
   (c) removing the extracting agent from the resulting tar-like 2-mercaptobenzothiazole-containing residue,
   (d) working up the residue by heating at a temperature of from 240° to 310° C., under a pressur of 0.3 to 10 MPa, after or during forcing in of hydrogen and/or hydrogen sulphide in the absence of any substantial amount of the starting material, to form a product mixture.
   (e) separating aniline and benzothiazole from the thus formed product mixture.
3. A process according to claim 1, wherein that aniline and benzothiazole are separated from the product mixture by vacuum distillation.
4. A process according to claim 1, further comprising at least partly removing aniline and benzothiazole, by vacuum distillation, before working up.

* * * * *

UNITED STATES PATENT AND TRADEMARK OFFICE
CERTIFICATE OF CORRECTION

PATENT NO. : 4,780,540
DATED : October 25, 1988
INVENTOR(S) : Gabriel Denecker, Guido Lahousse, Henri Vandebroek and Pol Bamelis It is certified that error appears in the above-identified patent and that said Letters Patent is hereby corrected as shown below:

On the title page, item [75], "Pol Balmelis" should be --Pol Bamelis--.
Correct the spelling of inventor Pol Bamelis.

Signed and Sealed this

Twelfth Day of December, 1989

Attest:

JEFFREY M. SAMUELS

Attesting Officer

Acting Commissioner of Patents and Trademarks